(12) United States Patent
Mantelmacher

(10) Patent No.: US 11,253,377 B2
(45) Date of Patent: Feb. 22, 2022

(54) PROSTHETIC SUSPENSION MOUNTING ASSEMBLY

(71) Applicant: H. Lee Mantelmacher, Owings Mills, MD (US)

(72) Inventor: H. Lee Mantelmacher, Owings Mills, MD (US)

(73) Assignee: Kiss Technologies, LLC, Owings Mills, MD (US)

( * ) Notice: Subject to any disclaimer, the term of this patent is extended or adjusted under 35 U.S.C. 154(b) by 288 days.

(21) Appl. No.: 15/708,801

(22) Filed: Sep. 19, 2017

(65) Prior Publication Data

US 2018/0008435 A1 Jan. 11, 2018

Related U.S. Application Data

(60) Division of application No. 14/809,907, filed on Jul. 27, 2015, now abandoned, and a continuation-in-part
(Continued)

(51) Int. Cl.
*A61F 2/60* (2006.01)
*A61F 2/78* (2006.01)
*A61F 2/80* (2006.01)

(52) U.S. Cl.
CPC ............... *A61F 2/78* (2013.01); *A61F 2/60* (2013.01); *A61F 2/7812* (2013.01); *A61F 2/80* (2013.01);
(Continued)

(58) Field of Classification Search
CPC ........................................................ A61F 2/80
See application file for complete search history.

(56) References Cited

U.S. PATENT DOCUMENTS 3,828,370 A * 8/1974 Ihmels .................... A41F 9/002
2/322
4,499,613 A * 2/1985 Yarrow ................. A61F 2/6607
623/48
(Continued)

OTHER PUBLICATIONS

Kohler et al. "A new in-built device for one-point stepless prosthetic alignment." Department of Orthopeaedic Surgery, Karolinski Hospital, Stockholm. Prosthetics and Orthotics International. 1998, 12, 103-104. (Year: 1988).*

*Primary Examiner* — Jacqueline Woznicki
(74) *Attorney, Agent, or Firm* — Royal W. Craig; Gordon Feinblatt LLC

(57) ABSTRACT

A prosthetic suspension-mounting system which employs an improved flathead bolt and socket centering cup combination for securement of an amputee-limb enveloping liner within a prosthesis. The liner has a strap fixedly attached on the bottom end of the liner by a flathead bolt. The mounting system also includes a containment socket for seating the liner in the prosthesis using the head of the flathead bolt as a bearing surface against a floor of the socket. The containment socket has a slot there through at a position corresponding to the strap of the liner. The socket is provided with a disk-shaped recess having a flat floor, and the liner is provided with a distal flathead bolt having a flat head to provide a direct bearing surface against the floor of the socket. This provides a delimited bearing surface to keep the liner substantially centered within the prosthesis while still affording a lateral degree of freedom to avoid concentration of lateral forces.

19 Claims, 4 Drawing Sheets

Related U.S. Application Data of application No. 14/373,059, filed as application No. PCT/US2012/069768 on Dec. 14, 2012, now Pat. No. 9,492,292.

(60) Provisional application No. 62/030,831, filed on Jul. 30, 2014, provisional application No. 61/570,584, filed on Dec. 14, 2011.

(52) U.S. Cl.
CPC ............ *A61F 2002/7831* (2013.01); *A61F 2002/7875* (2013.01); *A61F 2002/7881* (2013.01)

(56) References Cited

U.S. PATENT DOCUMENTS

| | | | | |
|---|---|---|---|---|
| 4,872,879 A | * | 10/1989 | Shamp | A61F 2/80 623/36 |
| 5,443,526 A | * | 8/1995 | Hoerner | A61F 2/76 411/531 |
| 5,888,233 A | * | 3/1999 | Randstrom | A61F 2/76 623/38 |
| 6,793,682 B1 | * | 9/2004 | Mantelmacher | A61F 2/7812 623/33 |

* cited by examiner

PROSTHETIC SUSPENSION MOUNTING ASSEMBLY

CROSS-REFERENCE TO RELATED APPLICATION(S)

The present application is a division of U.S. patent application Ser. No. 14/809,907 filed 27 Jul. 2015, which in turn derives priority from U.S. Provisional Patent Application No. 62/030,831 filed Jul. 30, 2014, and is a continuation-in-part of U.S. Ser. No. 14/373,059 filed effective Dec. 14, 2012, both of which are incorporated herein by reference in their entireties.

BACKGROUND OF THE INVENTION

1. Field of the Invention

The present invention relates to prosthetics and, more particularly, to a prosthetic suspension mounting assembly comprising an improved socket centering block or cup and liner bearing pin which combine to provide a more robust mounting solution for above-the-knee and below-the-knee amputation patients seeking a suspension-mount for their prosthetic limb.

2. Description of the Background

There are a variety of different types of prosthetic devices for patients that have had either transfemoral (above-knee) or transtibial (below the knee) amputation. Typically, post-operative prosthetic devices for either type of amputation begins with a liner that is rolled onto the residual limb. The liner is a soft, stretchy material that acts as an interface with the prosthesis.

Once the liner is on, the residual limb then slides into a hard socket. This socket is specially made to fit and can be made out of a variety of materials. The hard socket for a transfemoral prosthesis has a knee joint connected to it, and the more fluid and natural the movement of the knee the better. Transtibial prosthetics have no knee joint. In both cases (with of without a knee joint) there is typically an aluminum carbon fiber tube to which a foot module is connected.

For example, U.S. Pat. No. 5,653,786 to Naser issued Aug. 5, 1997 shows a prosthetic device 20 having a generally cylindrical socket 24 with an opening for receiving an amputated limb. The socket 24 is closed at the other end, and is mounted on a bendable knee joint. Once the limb is properly received within the socket 24, straps 38 are adjusted so that a secure fit is achieved. The patient then is able to walk using the prosthetic device 20.

With all such transfemoral and/or transtibial prosthetics (above & below the knee), it is very important that the socket be securely fitted to the limb and secured in place. Stability is a common problem as many existing anchoring systems use a single attachment point to hold the residual limb in place, and this typically leads to extraneous pivoting, rotation and shift during ambulation.

The prior art includes mechanical fixtures that lock the limb/liner in the socket. These typically include a socket molded into the distal end of the liner, and a pin threaded into the socket. The pin passes through the bottom of the socket and ratchet-locks into a base there below. U.S. Pat. No. 8,349,021 to Laghi et al. issued Jan. 8, 2013 gives an example.

The prior art ICEX® Socket System is a total surface bearing (TSB) socket that pulls the limb into the socket using a lanyard. The lanyard is connected to the liner through a slot in the bottom of the socket. The lanyard is pulled to allow the patient's residual limb, which is enclosed in the silicone liner, to be drawn into the socket by the lanyard. The lanyard is then anchored to the front of the socket.

There are also a number of "suction" type sockets that eliminate the lanyard. U.S. Pat. No. 6,645,253 to Caspars issued Nov. 11, 2003 shows a suction system that employs a vacuum pump to impart suction to the liner, the vacuum pump doubling as a shock absorber for the artificial limb. Commercially, this is known as the Harmony® System which pulls air from the sealed socket and evacuates moisture (sweat) buildup. A nonporous polyurethane liner (not shown) is fitted over the residual limb and is inserted in the socket. A vacuum pump is attached via a connector block beneath the socket to create a vacuum force which is coupled by a tube to the liner, thereby evacuating air and seating it to the residual limb. This provides a total-contact hypobaric suction equal weight distribution socket liner which tacks op to the skin of the residual limb and provides total contact with the limb.

There is also a "suspension" type socket that suspends the limb within the socket. U.S. Pat. No. 6,793,682 to the present inventor discloses a "Sure-fit Prosthetic Attachment System" (known commercially as the KISS® System) for transfemoral and/or transtibial prostheses, comprising a Liner for enveloping an amputee limb. The liner has a strap attached at one end to a reinforcement plate that is sewn, bonded, and/or attached with Velcro to the liner toward the top, and a buckle is attached to the other end of the strap and is suspended thereby from the liner. Another strap is fixedly attached to the bottom end of the liner. The anchoring system also includes a containment socket for seating the liner. The containment socket has a pair of slots there through at positions corresponding to the buckle and strap of the liner, respectively. To apply the anchoring system, the patient first applies the liner to his/her limb. The liner is then inserted into the socket with the fastening strap and buckle protruding oat through the respective slots. The fastening strap is then threaded up through the buckle (running upward along the side of the socket) and is inserted there through. The patient pulls down on the strap, which works by pulley action to draw the liner down into the socket until the liner is securely seated in the socket. When fully seated, the fastening strap is secured to itself by hook-and-loop. The foregoing forms a suspension which holds the prosthesis on. Moreover, the fastening straps through slots absolutely prevent lateral shift as well as rotation. On the other hand, the patient need only readjust the Hook-and-loop closure to adjust the position of the limb within the socket Thus, if the limb changes position because of volume change and the distal migration of the limb into the socket, the prosthesis can easily be adjusted to compensate. Note that the fastening strap is attached to the distal end of the liner by a button-head cap screw 43 that is seated within a recess 35 in the base. The button-head of cap screw 43 centers the liner but affords no lateral freedom at all, and effectively concentrates all lateral forces at the distal end of the liner. In addition, the base is required to have a compound recess 35 which is semi-circular (on one side) with a pronounced indentation 37 in the center tor seating the head of screw 43 on the liner 10. This compels a fairly thick base and large-profile mount.

One of the primary concerns of prosthesis design and construction is that the device be lightweight and provide a comfortable fit to the residual limb, and it is extremely important to emulate a natural gait when in use.

It would be more advantageous to provide a prosthetic mounting assembly that is lower in profile and which avoids concentrating lateral forces at a single point.

SUMMARY OF THE INVENTION

It is, therefore, an object of the present invention to provide a prosthetic suspension-mounting system that employs an improved flathead holt and socket centering block, also referred to as a centering cap or socket centering cup, combination for securement of the liner within the socket of the prosthesis.

In accordance with the above-described object, the present invention is a mounting system for a suspension-type transfemoral and/or transtibial prosthesis, including a liner for enveloping an amputee limb. The liner has a strap fixedly attached on the bottom end of the liner by a flathead bolt, and the head of the flathead bolt serves as a bearing surface. The mounting system also includes a containment socket for receiving and seating the liner and limb, and generally conforming thereto. In accordance with the invention, the socket is provided with a disk-shaped recess having a flat floor, and a puck- or disk-shaped centering cup is seated within the disk-shaped recess of the containment socket. The centering cup presents an upwardly-exposed, disk-shaped recess in which the flathead bolt sits, providing the opposing bearing surface. Both the centering cup and the socket have aligned slots there through at a position corresponding to the strap of the liner, to allow passage of the strap.

The flat head of the distal flathead bolt has a diameter smaller than that of the centering cup recess, preferably between one-half and one-fifth the diameter of recess, and most preferably about one-third the diameter. This provides a circularly-constrained bearing surface for the flat head of the distal pin, keeping it substantially centered and yet affording a lateral degree of freedom to avoid concentration of lateral forces at the distal end of the liner. In addition, the flat-head bolt submerged in the disk-shaped recess allows a lighter lower-profile mount.

To apply the anchoring system, the patient first applies the liner to his/her limb. The liner is then inserted into the socket with the fastening strap and buckle protruding out through the respective slots. The fastening strap is then threaded up through the buckle (mining upward along the side of the socket) and is inserted there through. The patient pulls down on the strap and it works by pulley action to draw the liner down into the socket until the liner is securely seated in the socket. When fully seated, the fastening strap is secured to itself by hook and loop.

The foregoing forms a suspension which holds the prosthesis on. Moreover, the fastening straps through slots absolutely deter lateral shift as well as rotation. On the other hand, the patient treed only readjust the hook and loop closure to adjust the position of the limb within the socket. Thus, if the limb changes position because of volume change and the distal migration of the limb into the socket, the prosthesis can easily be adjusted to compensate.

The above and other objects, features and advantages of the present invention will become readily apparent from the following detailed description thereof which is to be read in connection with the accompanying drawings.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Figure 1:
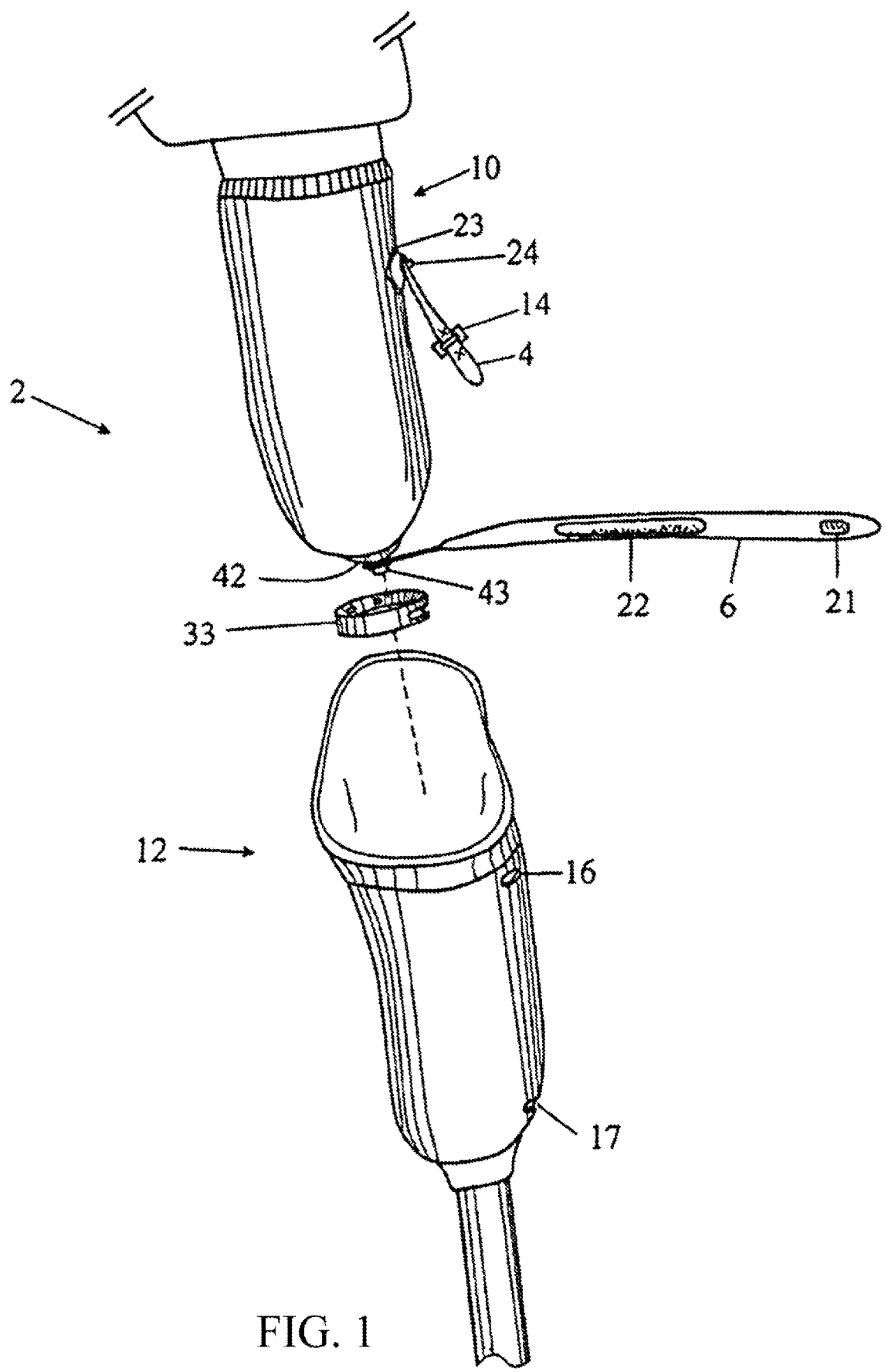
FIG. 1 is a perspective exploded illustration of the sure-fit prosthetic anchoring system 2 according to the present invention.

FIG. 1 is a perspective illustration of a sure-fit prosthetic anchoring system 2. The anchoring system 2 is adapted for a patient that has undergone a limb reduction surgery resulting in an above-the-knee amputation. In a preferred embodiment, the anchoring system 2 generally includes a commercially-available liner 10 equipped with upper and lower strap-anchors 4, 6, respectively. The upper strap anchor 4 is pivotally attached at one end by grommet-post 24 to a reinforcement plate 23, plate 23 being a plastic member that is sewn, bonded and/or attached with hook and loop peripherally onto the liner 10 at an upper outside position as shown. In a preferred embodiment the grommet-post 24 comprises two screw-together sections having 1' flanges which sandwich the plate 23 and upper strap 4 together. The other end of upper strap 4 bears a buckle 14 with a short length of extension strap past the buckle 14 to provide a finger-grip. The extension strap past the buckle 14 may be a short length of strap or plastic attached to the buckle itself, a slightly longer length sewn to the upper strap 4, or art even longer length of strap/plastic attached by the grommet-post directly to the reinforcement plate 23, in all cases serving to provide the user with a finger grip to pull the liner 10 down.

In addition, a lower strap 6 is attached at one end to the bottom of the liner 10 by a flathead machine bolt 43 as described below.

The liner 10 fits within a socket 12 and rests upon a centering cup 33. In a preferred embodiment, the socket 12 is formed with, at least one slot 16 passing through an upper side (at the outside of the limb) for allowing the upper strap 4 and buckle 14 to pass outwardly therefrom. The socket 12 is also formed with one lower slot 17 at the bottom and aligned with the upper socket 16 for allowing the lower strap 6 to pass outwardly therefrom.

The lower fastening strap 6 has a section 21 of hook-and-loop material at the distal end, and a mating section 22 of hook-and-loop material running lengthwise along its mid-section. Alternately, a single section of hook-and-loop material may run along the entire length of lower fastening strap 6. The hook and loop is preferably a hybrid weave with hook and loop being mixed together, so there is no distinction between the hook and loop sides. Such hook and loop features are commercially available from Velcro® USA. In use, the patient would first apply liner 10 to limb. The liner 10 is then inserted into the socket with lower fastening strap 6 threaded through centering cup 33 out through lower slot 17, and upper strap 4 with buckle 14 passing out through upper slot 16. The junction of the upper strap 4 with the liner 10 limits downward insertion of the liner 10 into the socket 12 and seats the liner 10 onto the centering cup 33 as explained below. Importantly, this constraint avoids hunching of the liner fabric whilst seating the liner 10, a very common problem with conventional liners/sockets. The lower fastening strap 6 is then threaded up through the protruding buckle 14 and downwardly, and the strap 6 is pulled tight until the liner 10 is securely seated in the socket 12 atop centering cup 33. The fastening strap 6 is secured onto itself by joining the two sections 21, 22 of hook-and-loop material (or the one continuous section) in a loop. The foregoing forms a suspension which holds the prosthesis on and absolutely prevents lateral movement, pivotal shifting, and rotation. On the other hand, the simple hook-and-loop-attached strap 6 allows for convenient adjustment of the position of the limb within the socket 12. Thus, if the limb changes position because of volume change and the distal migration of the limb into the socket, the prosthesis can easily be adjusted by adjusting straps 4, 6 to compensate.

In an alternate embodiment, upper strap 4 with buckle 14 is not attached to liner 10, but is attached directly to the exterior surface of socket 12 above slot 17 for fastening strap 6. Slot 16 may thus be eliminated in this embodiment. As in previous embodiments, strap 4 may be pivotally attached at an upper outside position of socket 12 above slot 17 by a grommet-post to a reinforcement plate, which may be a plastic member that is sewn, bonded and/or attached with hook-and-loop to socket 12. However, upper strap 4 may also be attached directly to socket 12 using any available means known in the art and capable of providing a secure connection. In the present embodiment, to use the device, the patient would first apply liner 10 to limb. The liner 10 is then inserted into the socket with lower fastening strap 6 threaded through centering cup 33 out through lower slot 17. The lower fastening strap 6 is then threaded up through buckle 14, which is attached via strap 4 to an exterior surface of socket 12 above slot 17, and downwardly, and the strap 6 is pulled tight until the liner 10 is securely seated in the socket 12 atop centering cup 33. The fastening strap 6 is secured onto itself by joining the sections 21, 22 of hook-and-loop material. As with the foregoing embodiment, the instant connection system forms a suspension which holds the prosthesis on and absolutely prevents lateral movement, pivotal shifting, and rotation, while the simple hook-and-loop-attached strap 6 allows for convenient adjustment of the position of the limb within the socket 12. Thus, if the limb changes position because of volume change and the distal migration of the limb into the socket, the prosthesis can easily be adjusted by adjusting strap 6 within buckle 14 to compensate.

Liner 10 is largely a standard transfemoral or transtibial suspension liner designed for amputees with amputations along the length of the tibia or femur. There are a variety of commercially-available suspension liners which will suffice, provided that they afford good suspension independent of volume fluctuations and provide a comfortable anatomical fit. These liners are typically formed of silicone or a gel blend with or without a fabric shell, and they may be equipped with a threaded socket assembly 42 at the bottom end for screw-insertion of flathead machine bolt 43 (or more conventional locking pin as known in the art). As disclosed in applicant's prior U.S. Pat. No. 6,793,682, the disclosure of which is hereby incorporated by reference in its entirety, the otherwise conventional liner is preferably modified by tethering buckle 14, via upper strap 4, on the outwardly facing side of the liner 10. Strap 4 is secured to the liner 10 by first sewing, gluing and/or attaching with Velcro the reinforcement plate 23 peripherally to the shell of the lifter 10, and then passing a grommet-post 24 through the tip of the upper strap 4 and through the plate 23, thereby pivotally anchoring strap 4 thereto. In other embodiments, as described above, the strap 4 may be attached directly to an exterior surface of socket 12.

Strap 4 may be a short length (approximately 6") of braided Nylon or Dacron strap that is looped around one side of a rectangular buckle 14, thereby suspending buckle 14 approximately 3-5" downward from grommet-post 24 on liner 10 or socket 12. The buckle 14 is a simple rectangular stirrup-type stainless fixture. It should be understood that alternate embodiments are possible without departing from the scope and spirit of the invention, the point being that the tethered buckle 14 must be suspended by a short distance. In a preferred embodiment, a short length (approximately 1-2") of strap material is attached to the opposing side of buckle 14 in a like manner and extends therefrom to provide a finger-grip to facilitate insertion of the strap 4 and buckle 14 through the upper slot 16 in socket 12.

In addition to the upper strap 4 with buckle 14, in a preferred embodiment the liner 10 is equipped with a lower fastening strap 6 comprising approximately a 2' length of Nylon or Dacron braided strap attached at one end to, the bottom of liner 10. As stated previously, liner 10 may be equipped with a threaded socket assembly 42 at the bottom end which includes a threaded metal screw-socket embedded in a concave robber cup which is then epoxied and/or sewn, or otherwise fixedly attached to the lower distal end of the liner 10.

Figure 2:
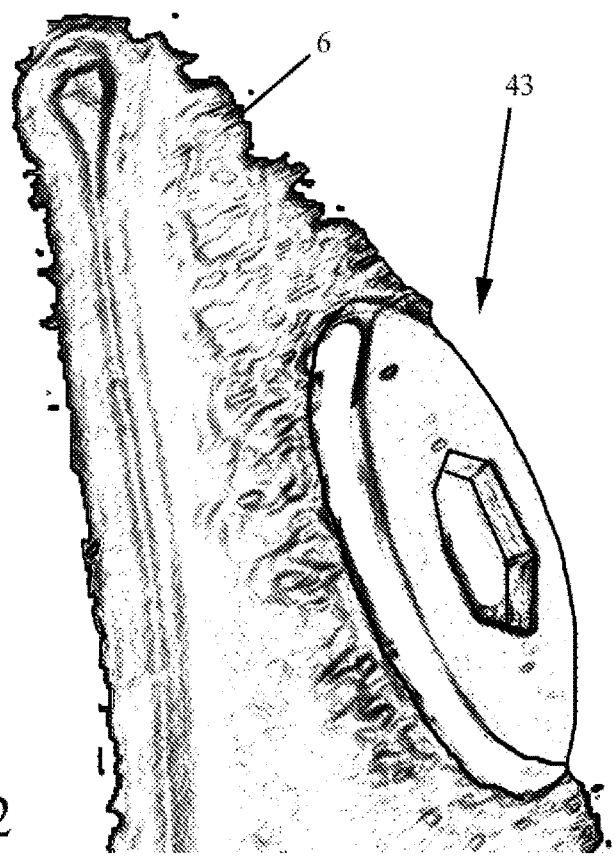
FIG. 2 is a close-up perspective view of the flat head bolt.

As seen in FIG. 2, the lower strap 6 is doubled over at one end and a flathead machined hex drive bolt 43 is passed through the strap 6 and is screwed into the threaded socket assembly 42 to anchor the strap 6 to the liner 10. The flathead hex drive bolt 43 may, for example, be a M10×12 12.9 thread flat bead stainless bolt having an oversized flat head with diameter at least twice that of the shaft, the head preferably having rounded edges as shown. In accordance with the invention, bolt 43 not only attaches strap 6 to liner 10, but also serves as a bearing surface against centering cup 33 as will be described. The lower fastening strap 6 has a section 21 of hook-and-loop material attached to the distal end, and a mating section 22 of hook-and-loop material running lengthwise along its mid-section for attaching strap 6 onto itself around buckle 14 (see FIG. 1).

Socket 12 is generally a conventional socket formed of flexible plastic that is vacuum formed. The socket 12 made in a custom-fitted component that is made in a conventional manner of a copolymer plastic, plastic polypropylene, polyester, acrylic/epoxy resin. The socket 12 may be vacuum formed or thermoformed by heating the plastic material and forming it over a mold. In a preferred embodiment, socket 12 is formed with an upper pass-through slot 16 along the outside. Alternatively, a series of parallel pass-through slots 16 may be provided to facilitate adjustment. The upper slot(s) 16 is positioned with respect to the liner 10 inserted therein so that it/they align with the upper strap 4. Specifically, when the liner 10 is fully inserted, the pass-through slot 16 should be even level with the grommet-post 24 on liner 10. Other pass-through slots 16B, C . . . may be positioned slightly above or below for adjustment. This allows the tethered buckle 14 to be inserted directly through a slot 16 from inside the socket 12 to outside, such that downward tension on strap 4 anchors the grommet-post 24 directly against the slot 16. In other embodiments, strap 4 with buckle 14 may be attached to the exterior surface of socket 12 via reinforcement plate 23 and grommet 24 as described herein.

In addition to the upper slot(s) 16, a lower pass-through slot 17 is positioned downwardly along the same side of the socket 12 in a preferred embodiment. The pass-through slot 17 is spaced in line with a centering cup slot 38 (described below) with respect to the bottom of the socket 12. This way, when the liner 10 is fully inserted, the pass-through slot 17 allows the lower fastening strap 6 to be inserted there through.

The outer end of the socket 12 is adapted to be connected to a conventional, bendable knee joint (a variety of which are presently available) as seen in FIG. 1.

Figure 3:
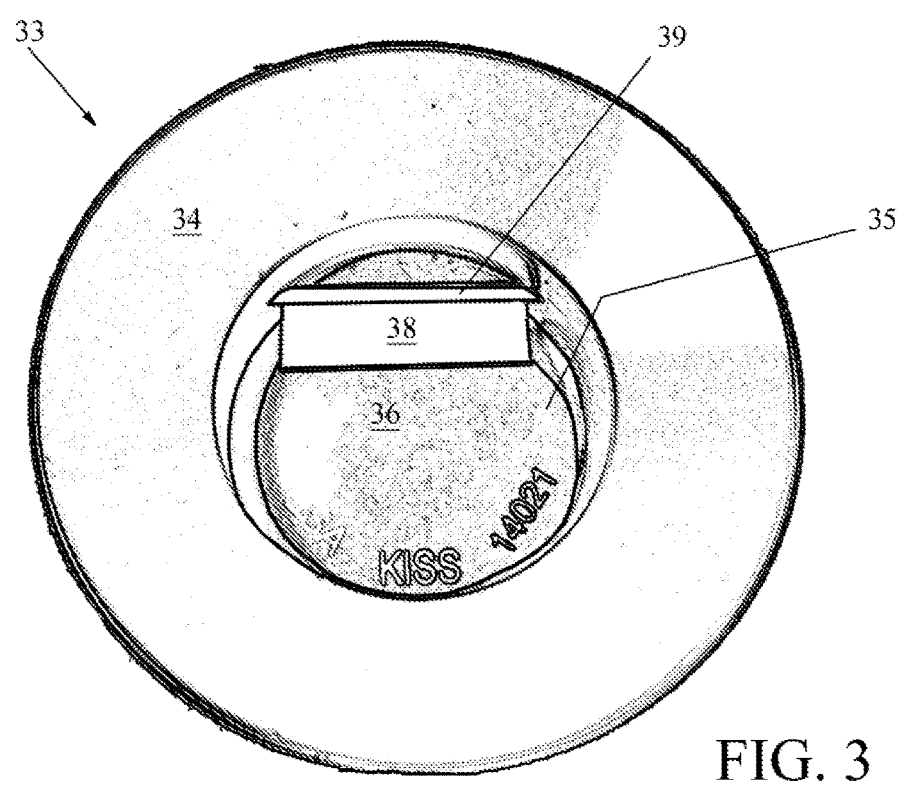
FIG. 3 is a close-up top view of the centering cup.
Figure 5:
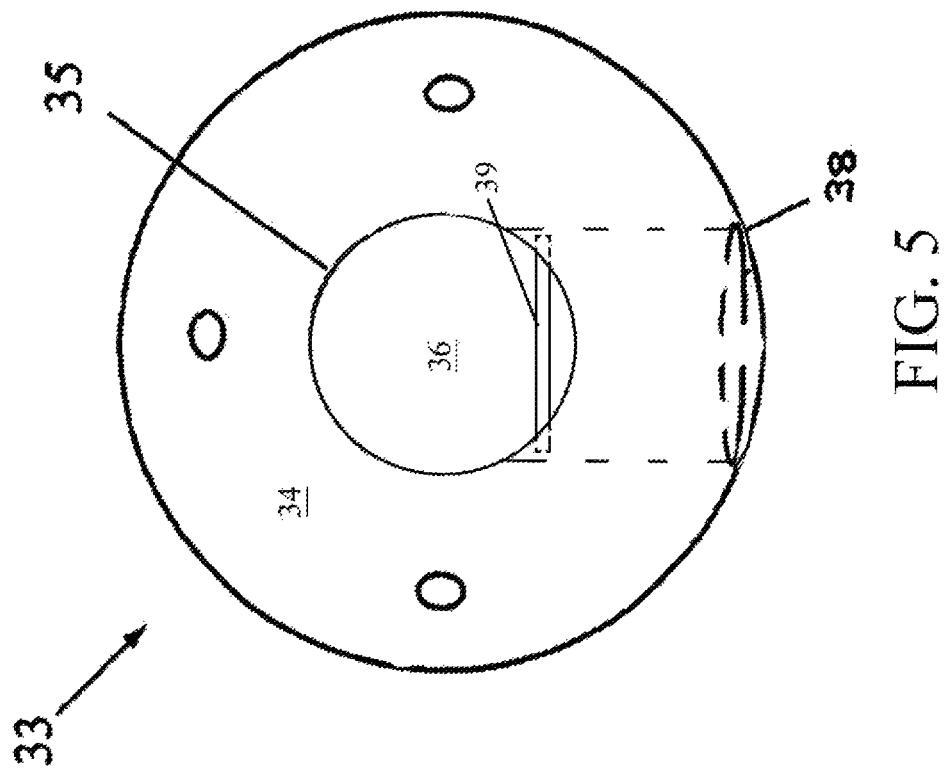
FIG. 5 is a close-up top cross-section of the centering cup.
Figure 4:
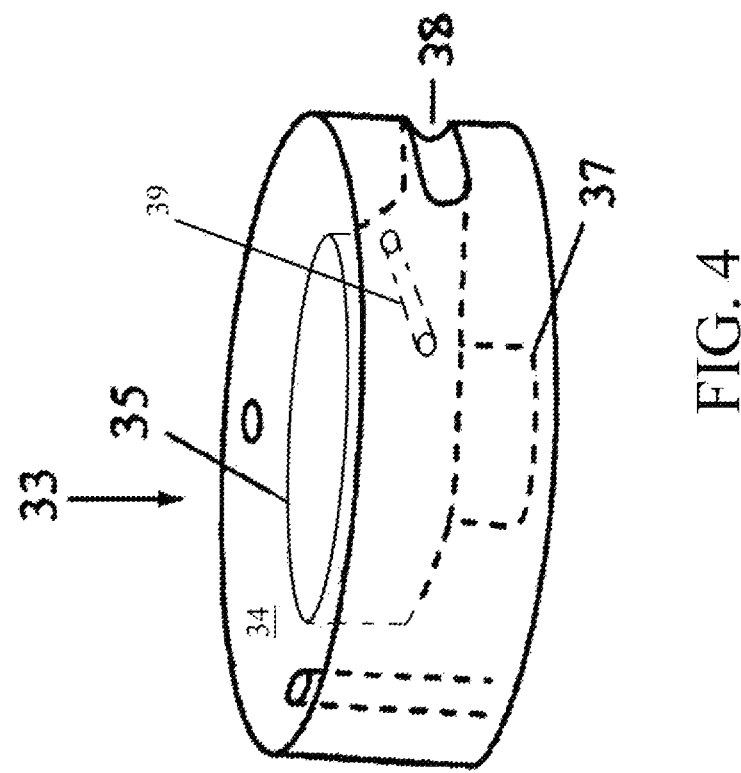
FIG. 4 is a close-up side cross-section of the centering cup.

FIGS. 3-5 are a top view, side internal diagram, and top internal diagram, respectively, of the centering cup 33 insert as in FIG. 1 which is attached internally to the bottom center of the socket 12. The centering cup 33 is a puck-like member preferably formed of Delrin®, aluminum, or other sturdy lightweight composite material. In accordance with the invention, centering cup 33 is formed with a concave upper rim 34 leading into a central circular recess 35. The concave upper rim 34 helps to seat and center the liner 10. The recess 35 is substantially circular and defined by a perfectly flat floor 36. The diameter of recess 35/floor 36 is preferably within a range of from 2-4 times that of the oversized flat head hex drive bolt 43, and most preferably approximately three times the diameter. The floor 36 effectively forms a "delimited" bearing surface for the flat head of bolt 43, e.g., constraining the bolt 43 to within a circular degree of freedom limited by the walls of recess 35.

The recess 35 is interrupted on one side by a slot 38 through which the lower fastening strap 6 is passed. Slot 38 continues out through the side of centering cup 33 and aligns with the lower slot 17 of socket 12 to pass the lower strap 6 outward. A roller pin 39 straddles the slot 38, and is journaled into the sidewalls of recess 35 suspended slightly above the floor 36 to guide and ease insertion of the strap 6 into slot 38 when the wearer dons the prosthesis. To apply the anchoring system 2, the patient first applies the liner 10 to his/her residual limb. The liner 10 is then partially inserted into the socket 32 until lower fastening strap 6 can be threaded through the slot 38 in centering cup 33 and on outward through the lower slot 17 through socket 12. In addition, the upper fastening strap 4 and buckle 14 may be passed outward through slot 16, in embodiments where fastening strap 4 and buckle 14 are attached directly to liner 10. The lower fastening strap 6 is then threaded up through the buckle 14 (strap 6 running upward along the side of the socket 12) and is inserted there through. The patient pulls down on the distal end of lower strap 6 which works by pulley action to draw the liner 10 down into the socket 12 until the liner 10 is securely seated in the socket 12. When fully seated the lower fastening strap 6 is secured to itself by joining the sections 21, 22 of hook-and-loop material. The lower fastening strap 6 through lower slot 17 forms a first anchoring point, and in a preferred embodiment, upper strap 4 through upper slot 16 forms a second anchoring point, the combination of the two anchoring points serving to reduce lateral movement pivotal and proximal shift, and rotation. When such motion does occur, the delimited bearing surface of floor 36 partially supports the liner 10 on the flat head of bolt 43 yet gives it a lateral degree of sliding freedom (limited by the walls of recess 35) which avoids concentration of lateral forces at the distal end of the liner 10. This effectively results in a "modified" suspension mount, the liner 10 being partially suspended by upper and lower straps 4, 6, centered and partially supported by the concave tipper rim 34 of centering cup 33, yet still being able to articulate therein in a ball-and-socket manner, and partially supported on the flat head of bolt 43 as it hears against floor 36, yet still being able to shift therein within a limited degree of freedom.

Importantly, the flat bearing surface of the low profile flat head belt 43 and flat floor 36 of the centering cup 33 combine to create the lowest profile attachment available for a residual-to-prosthetic socket using a gel liner with distal attachment. A primary goal when fabricating a transfemoral prosthesis is to be able to match the height of the anatomical knee center to the prosthetic knee center for a symmetrical gait as well as for cosmetic appearance. This is important during ambulation and when the individual is sitting. The present lower profile design is essential when fabricating a transfemoral prosthesis for an individual with a very long residual limb to obtain the stated results.

The resulting modified suspension mount is more fluid and helps to closely mimic the natural movement of the knee, resulting in a more comfortable and natural prosthetic. When desired, the patient need only readjust the hook-and-loop closures to adjust the position of the limb within the socket 12. Thus, if the limb changes position because of volume change and the distal migration of the limb into the socket, the prosthesis can easily be adjusted to compensate. Once the limb is properly received within the socket 12 and the straps 6 or 4 and 6 are appropriately adjusted so that a secure fit is achieved.

In addition, the flat-head bolt 43 seated in the shallow disk-shaped recess 35 allows a lighter lower-profile mount.

Importantly, the modified suspension mount with strap 6 passing directly sideward out through slot 38 across flat floor 36 beneath roller pin 39 also avoids catching and/or entanglement of the strap 6.

If desired, a plurality of through-bores may be formed axially through the upper rim 34 for screw-attachment through the socket 12 into the base of the bendable knee joint (transfemoral) or the base of the shaft (transtibial), either of which are typically attached directly beneath the socket 12. Alternatively, the through-bores may be eliminated and the centering cup 33 formed instead with a downwardly threaded hub for screw-attachment to the underlying base beneath socket 12.

Figure 6:
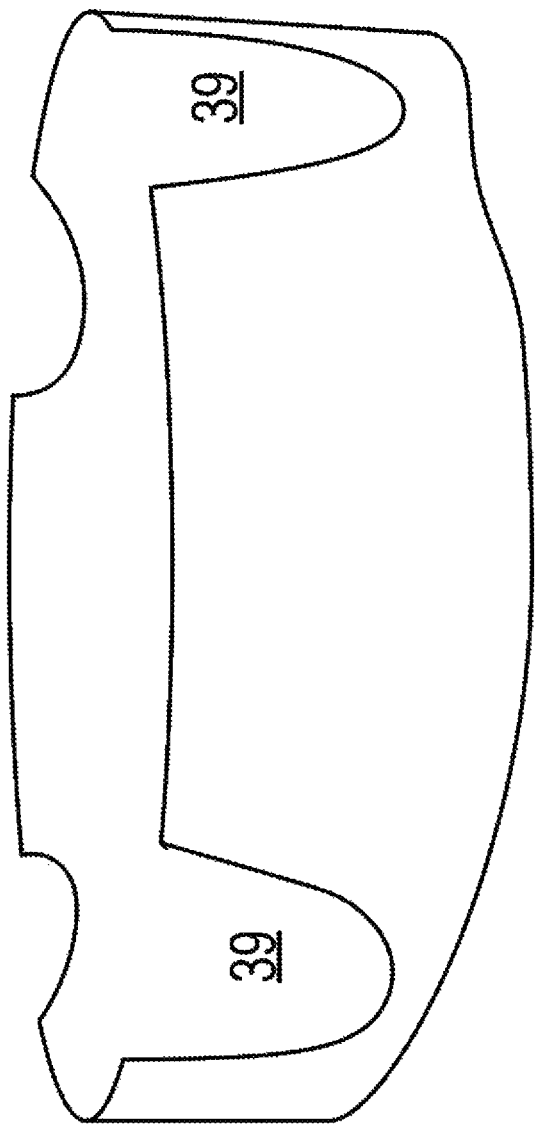
FIG. 6 is a close-up side view of the centering cup with optional crescent grooves designed to lock it into a thermoplastic/laminated socket without screws.

As an alternative to through-bores/screws, FIG. 6 is a close-up side view of a centering cup 33 with optional crescent grooves 39 designed to fixate the centering cup 33 inside a thermoplastic/laminated socket 12 without need of screws. In this case the peripheral walls of centering cup 33 are indented at a plurality (preferably four) evenly-spaced radial locations with fingernail-shaped "crescent" notches 39 tapered downward and opening upward toward concave upper rim 34. The thermoplastic/laminated socket 12 may be formed with conforming outward protrusions keyed thereto, which effectively orient and index the socket 12 and liner 10. This eliminates the need for without need for screw-fixation. The prosthetic anchoring system 2 described herein increases the stability of the liner anchor using the combined top-side and lower attachments to reduce extraneous up and down motion, pivotal and proximal shift, and rotation. When such motion does occur the specific configuration of the centering cup 33 and flathead bolt 43 comfortably accommodates it.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An anchoring system for securing a prosthetic liner inside a socket, comprising:
    a centering cup seated in said socket for seating said liner thereon, said centering cup comprising a disk formed with a concave top rim encircling a circular recess, said circular recess having a flat recessed circular floor having a first diameter; and
    a weight-bearing flathead bolt screwed into a distal end of said liner and having a flat circular head of a second diameter at least 50% smaller than said first diameter, the flat head of said bolt slidably contacting the flat recessed circular floor of said circular recess and constrained to slide thereon within a limited degree of sliding freedom limited to said first diameter.

2. The anchoring system of claim 1, wherein said liner comprises a lower attachment strap attached at a lower distal end.

3. The anchoring system of claim 2, wherein said centering cup comprises a sidelong groove passing through said centering cup into said circular recess for passing said lower attachment strap.

4. The anchoring system of claim 3, wherein said liner comprises an upper attachment strap attached above said lower attachment strap.

5. The anchoring system of claim 4, wherein said upper attachment strap is attached to said liner by a grommet-post.

6. The anchoring system of claim 5, wherein said grommet-post comprises at least two flat rim components sandwiching a first end of said upper fastening strap.

7. The anchoring system of claim 4, wherein said upper attachment strap comprises a hybrid weave hook and loop material.

8. The anchoring system of claim 4, wherein said upper attachment strap comprises a buckle.

9. The anchoring system of claim 8, wherein said buckle is a rectangular, stirrup-type stainless fixture.

10. The anchoring system of claim 3, wherein said centering cup includes a roller pin mounted proximate said sidelong groove therein.

11. The anchoring system of claim 10, wherein said roller pin is suspended above the flat recessed floor by opposing walls of said circular recess.

12. The anchoring system of claim 10, wherein said lower attachment strap is adapted to pass under the roller pin, through the sidelong groove and through an aligned attaching member slot.

13. The anchoring system of claim 1, wherein said centering cup is a plastic member.

14. The anchoring system of claim 1, wherein said liner further comprises a threaded socket assembly fixedly attached to the lower distal end of the liner and to which said flathead bolt is attached.

15. The anchoring system of claim 14, wherein said threaded socket assembly comprises a threaded metal screw socket embedded in a concave rubber cup.

16. The anchoring system of claim 1, wherein said second diameter is within a range of from one-half to one-fifth of said first diameter of said circular recess is at least two times the size of the flat head bolt.

17. The anchoring system of claim 1, wherein said centering cup comprises a plurality of radially-spaced grooves for indexing the centering cup within said socket.

18. The anchoring system of claim 1, wherein said flathead bolt being configured to bear against the flat floor of said recess comprises a head of said flathead bolt directly engaging said flat floor of said recess when said liner is inserted into said socket.

19. An anchoring system for securing a prosthetic liner inside a socket, comprising:
    a centering cup seated in said socket for seating said liner thereon, said centering cup comprising a disk formed with a concave top rim encircling a circular recess, said circular recess having a flat circular recessed floor of a first diameter defining a circularly-constrained bearing surface; and
    a weight-bearing flathead bolt screwed into a distal end of said liner, said flathead bolt having a flat circular head protruding from said liner and configured to bear weight against the flat floor of said recess, said flat circular head having a second diameter at least 50% smaller than said first diameter, the flat circular head of said bolt slidably contacting the flat circular recessed floor of said centering cup recess and constrained to slide thereon within a limited degree of sliding freedom limited to said first diameter.

* * * * *